United States Patent
Vester-Boler et al.

(10) Patent No.: US 11,311,028 B2
(45) Date of Patent: Apr. 26, 2022

(54) ORAL COMPOSITIONS AND METHODS FOR ANIMALS

(71) Applicant: Societe des Produits Nestle S A, Vevey (CH)

(72) Inventors: Brittany M. Vester-Boler, St. Louis, MO (US); Julie K Spears, St. Louis, MO (US)

(73) Assignee: SOCIÉTÉ DES PRODUITS NESTLÉ S.A., Vevey (CH)

(*) Notice: Subject to any disclaimer, the term of this patent is extended or adjusted under 35 U.S.C. 154(b) by 410 days.

(21) Appl. No.: 16/376,020

(22) Filed: Apr. 5, 2019

(65) Prior Publication Data

US 2019/0307822 A1    Oct. 10, 2019

Related U.S. Application Data

(60) Provisional application No. 62/654,626, filed on Apr. 9, 2018.

(51) Int. Cl.

| | |
|---|---|
| *A61K 36/02* | (2006.01) |
| *A23K 10/16* | (2016.01) |
| *A23K 10/20* | (2016.01) |
| *A23K 10/30* | (2016.01) |
| *A61K 35/644* | (2015.01) |
| *A61K 8/99* | (2017.01) |
| *A61Q 11/00* | (2006.01) |
| *A61K 8/98* | (2006.01) |
| *A23K 20/163* | (2016.01) |
| *A61K 35/00* | (2006.01) |
| *A23K 50/40* | (2016.01) |
| *A61K 35/748* | (2015.01) |
| *A23K 50/42* | (2016.01) |

(52) U.S. Cl.
CPC ............. *A23K 10/16* (2016.05); *A23K 10/20* (2016.05); *A23K 10/30* (2016.05); *A23K 20/163* (2016.05); *A23K 50/40* (2016.05); *A61K 8/988* (2013.01); *A61K 8/99* (2013.01); *A61K 35/00* (2013.01); *A61K 35/644* (2013.01); *A61K 35/748* (2013.01); *A61K 36/02* (2013.01); *A61Q 11/00* (2013.01); *A23K 50/42* (2016.05)

(58) Field of Classification Search
None
See application file for complete search history.

(56) References Cited

U.S. PATENT DOCUMENTS

2008/0131561 A1    6/2008    Patanawongyuneyong

FOREIGN PATENT DOCUMENTS

| CN | 101264235 A | 9/2008 |
|---|---|---|
| CN | 102048225 A | 5/2011 |
| WO | 2011027301 A1 | 3/2011 |

OTHER PUBLICATIONS

Website document entitled: "7 Natural Remedies to Cure Your Dog's Bad Breath" by Nicole Shein Mar. 17, 2020. available at www.thisdogslife.co/7-natural-remedies-to-cure-your-dogs-bad-breath. Downloaded Sep. 27, 2021. (Year: 2020).*
Website document entitled "Dentalife ActivFresh Daily Oral Care Large Dental Dog Treats". Available at www.chewy.com/dentalife-activfresh-daily-oral-care/dp/183287. Downloaded Sep. 27, 2021. (Year: 2021).*
Raskin et al. (2004) Current Pharmaceutical Design, 10, 3419-3429. (Year: 2004).*
Tallarida (2011) Genes and Cancer, 2(11): 1003-1008. (Year: 2011).*
XP002609376 "Spirulina Honey", CNPD Nov. 1, 2006.
XP002792476 URL:https://www.dogsnaturallymagazine.com/benefits-of-spirulina Jun. 16, 2011.
PCT/IB2019/052824, International Search Report, dated Jun. 28, 2019.

* cited by examiner

*Primary Examiner* — Russell G Fiebig

(57) ABSTRACT

The present invention is directed to methods and compositions for treating, preventing, or minimizing bad breath in an animal, including administering compositions comprising honey and spirulina.

7 Claims, No Drawings

ORAL COMPOSITIONS AND METHODS FOR ANIMALS

CROSS REFERENCE TO RELATED APPLICATIONS

This application claims priority to U.S. Provisional Application Ser. No. 62/654,626 filed Apr. 9, 2018, the disclosure of which is incorporated in its entirety herein by this reference.

BACKGROUND

Halitosis is a common ailment among animals including humans and companion animals. As all pet owners are aware, the smell of a pet's breath can be rank enough to repulse the pets' owners, as well as the owners' friends and relatives, thereby adversely affecting the emotional bond between dog and human. Remedies, such as mouthwashes, pastes, and gels, exist for use in combating halitosis as well as "fresheners," i.e., cover-up liquids and solids, which can be administered to humans or companion animals. Additionally, chemical sprays and cleansers can be applied to an oral cavity to combat bad breath.

However, "fresheners" generally do nothing more than temporarily mask the problem of bad breath in animals. Additionally, various fresheners, mouthwashes, gels, and the like can contain active substances that are not always desirable such as alcohols and zinc compounds.

To the extent that offensive odors arise from the oral cavity alone, scraping of plaque and tartar buildup from the animal's teeth is a known remedy, though one usually requiring the expertise and expense of a dental practitioner or veterinarian. While tartar and plaque removal can be effective and beneficial from a dental perspective, the offensive odors from the animal's mouth are neither entirely eliminated, nor even reduced for an appreciable amount of time. Such scraping does not eliminate the odor-causing bacteria, but only a particular breeding place for such bacteria.

Therefore, research and development of oral care compositions and methods for humans and companion animals continued to be sought.

SUMMARY

The present disclosure relates to methods and compositions comprising honey and spirulina. Such methods and compositions can be used to treat, prevent, or minimize bad breath in an animal.

The present inventors have discovered that a composition containing honey and spirulina can provide synergistic effects for controlling bad breath in an animal. Such effect can help treat such animals suffering from halitosis. Accordingly, a method for treating, preventing, or minimizing bad breath in an animal can comprise orally administering a composition comprising honey and spirulina to the animal.

Additionally, a composition for treating, preventing, or minimizing bad breath in an animal can comprise honey and *spirulina*.

Additional features and advantages are described herein and will be apparent from, the following Detailed Description.

DETAILED DESCRIPTION

Definitions

Some definitions are provided hereafter. Nevertheless, definitions may be located in the "Embodiments" section below, and the above header "Definitions" does not mean that such disclosures in the "Embodiments" section are not definitions.

As used in this disclosure and the appended claims, the singular forms "a," "an" and "the" include plural referents unless the context clearly dictates otherwise. The term "and/or" used in the context of "X and/or Y" should be interpreted as "X," or "Y," or "X and Y." Where used herein, the term "example," particularly when followed by a listing of terms, is merely exemplary and illustrative, and should not be deemed to be exclusive or comprehensive.

As used herein, "about" is understood to refer to numbers in a range of numerals, for example the range of −10% to +10% of the referenced number, preferably within −5% to +5% of the referenced number, more preferably within −1% to +1% of the referenced number, most preferably within −0.1% to +0.1% of the referenced number. A range that is "between" two values includes those two values. Furthermore, all numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

All percentages expressed herein are by weight of the total weight of the composition on a dry matter basis unless expressed otherwise. When reference is made to the pH, values correspond to pH measured at 25° C. with standard equipment.

The term "halitosis" refers to unpleasant odor that is present on the breath of an animal and can be interchangeably used with the term "bad breath." In one various aspects, halitosis can refer to the bad breath of a human, a companion animal, or even a dog.

The term "honey" refers to any type of honey produced by any type of bee from any type of floral source, or any other source, in any region of the world. In one embodiment, the honey can include polyfloral honey, monofloral honey, or honeydew honey.

In another embodiment, the honey can be selected from the group consisting of clover honey, manuka honey, sourwood honey, buckwheat honey, rosemary honey, dandelion honey, acacia honey, eucalyptus honey, alfalfa honey, avocado honey, basswood honey, blueberry honey, orange blossom honey, sage honey, and mixtures thereof.

The term "*spirulina*" refers to a dried biomass of cyanobacteria (blue-green algae) that can be consumed by humans and other animals, and includes *Arthrospira platensis* and/or *Arthrospira maxima*.

The terms "food," "food product" and "food composition" mean a product or composition that is intended for ingestion by an animal and provides at least one nutrient to the animal. The term "pet food" means any food composition intended to be consumed by a companion animal.

The term "animal" refers to any animal that could benefit from one or more of the compositions or methods of the present invention including human, avian, bovine, canine, equine, feline, hircine, lupine, murine, ovine, and porcine animal.

The term "companion animal" means a dog or a cat. As used herein, the term "dog" and "canine" can be used interchangeably. As used herein, the term "cat" and "feline" can be used interchangeably. In one embodiment, the companion animal can be a canine.

"Wet food" means a pet food having a moisture content from about 50% to about 90%, and in one aspect, from about 70% to about 90%. "Dry food" means a pet food having a moisture content less than about 20%, and in one aspect, less than about 15%, and in a specific aspect, less than about 10%. "Semi-moist food" means a pet food having a moisture content from about 20% to about 50%, and in one aspect, from about 25% to about 35%. "Kibbles" means pieces of dry or semi-moist pet food which can have a pellet shape or any other shape. Non-limiting examples of kibbles include particulates; pellets; pieces of pet food, dehydrated meat, meat analog, vegetables, and combinations thereof; and pet snacks, such as meat or vegetable jerky, rawhide, and biscuits.

The term "dietary supplement" or "supplement" means a product that is intended to be ingested in addition to the normal animal diet. Dietary supplements may be in any form, e.g., solid, liquid, gel, tablets, capsules, powder, and the like. In one aspect, they can be provided in convenient dosage forms. In some embodiments, they can be provided in bulk consumer packages such as bulk powders, liquids, gels, or oils. In other embodiments, supplements can be provided in bulk quantities to be included in other food items such as snacks, treats, supplement bars, beverages and the like.

The compositions disclosed herein may lack any element that is not specifically disclosed herein. Thus, a disclosure of an embodiment using the term "comprising" includes a disclosure of embodiments "consisting essentially of" and "consisting of" the components identified. Similarly, the methods disclosed herein may lack any step that is not specifically disclosed herein. Thus, a disclosure of an embodiment using the term "comprising" includes a disclosure of embodiments "consisting essentially of" and "consisting of" the steps identified. Moreover, the description of some steps as "optional" does not imply that the other steps which are not explicitly described as optional are necessarily required.

Any embodiment disclosed herein can be combined with any other embodiment disclosed herein.

"Prevention" includes reduction of risk and/or severity of a condition or disorder. The terms "treatment," "treat" and "to alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment," "treat" and "to alleviate" are also intended to include the potentiation or otherwise enhancement of one or more primary prophylactic or therapeutic measure. The terms "treatment," "treat" and "to alleviate" are further intended to include the dietary management of a disease or condition or the dietary management for prophylaxis or prevention a disease or condition. A treatment can be patient- or doctor-related.

The relative terms "improved," "increased," "enhanced" and the like refer to the effects of the composition disclosed herein (a composition comprising honey and *spirulina* or a prophylactic dose of honey and *spirulina*) relative to a composition not having honey and *spirulina*, or lacking either honey or *spirulina*, but otherwise identical.

The term "therapeutically effective amount" means an amount of a compound of the present invention that (i) treats or prevents the particular disease, condition, or disorder, (ii) attenuates, ameliorates, or eliminates one or more symptoms relating thereto of the particular disease, condition, or disorder, or (iii) prevents or delays the onset of one or more symptoms of the particular disease, condition, or disorder described herein. In one embodiment, therapeutically effect amount can refer to the amount to treat bad breath.

The term "long-term administration" means periods of repeated administration or consumption in excess of one month. Periods of longer than two, three, or four months can be used for certain embodiments. Also, more extended periods can be used that include longer than 5, 6, 7, 8, 9, or 10 months. Periods in excess of 11 months or 1 year can also be used. Longer term use extending over 1, 2, 3, or more years are included in the invention. For certain animals, the animal can continue consuming on a regular basis for the remainder of its life. This can also be referred to as consumption for "extended" periods.

The term "regular basis" or "regular administration" means at least monthly dosing with the compositions or consumption of the compositions, and in one aspect, means at least weekly dosing. More frequent dosing or consumption, such as twice or three times weekly, can be performed in certain embodiments. Still, in other embodiments, regimens can be used that comprise at least once daily consumption. The skilled artisan will appreciate that feeding amounts will be a function of the composition that is being consumed or administered as well as the animal consuming the food, and some food compositions may require more or less frequent administration to maintain a desired level or acceptable breath odor.

All patents, patent applications, publications, technical and/or scholarly articles, and other references cited or referred to herein are in their entirety incorporated herein by reference to the extent allowed by law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved.

Embodiments

The present disclosure relates to methods and compositions comprising honey and *spirulina*. Such methods and compositions can be used to treat, prevent, or minimize bad breath in an animal.

The present inventors have discovered that a composition containing honey and *spirulina* can provide synergistic effects for controlling bad breath in an animal. Such effect can help treat such animals suffering from halitosis. Accordingly, a method for treating, preventing, or minimizing bad breath in an animal can comprise orally administering a composition comprising honey and *spirulina* to the animal.

Additionally, a composition for treating, preventing, or minimizing bad breath in an animal can comprise honey and *spirulina*. Generally, the honey can be any type of honey. In one embodiment, the honey can include polyfloral honey, monofloral honey, or honeydew honey. In another embodiment, the honey can be selected from the group consisting of clover honey, manuka honey, sourwood honey, buckwheat honey, rosemary honey, dandelion honey, acacia honey, eucalyptus honey, alfalfa honey, avocado honey, basswood honey, blueberry honey, orange blossom honey, sage honey, and mixtures thereof. Generally, the *spirulina* can be any type of *spirulina*. In one embodiment, the *spirulina* can be dried form of cyanobacteria (blue-green algae) that includes *Arthrospira platensis* and/or *Arthrospira maxima*.

Generally, the honey can be present in any therapeutically effect amount to controlling bad breath in an animal when combined with *spirulina* and generally depends on the form of composition to be administered. In a general embodiment, the honey can present in an amount of about 0.001 wt % to about 50 wt % of the composition. In some aspects, when the composition is a treat, the honey can be present in an amount of about 0.001 wt % to about 50 wt % of the treat, or even about 0.5 wt % to about 15 wt % of the treat, or in one specific aspect, about 1 wt % to about 5 wt %. In other aspects, when the composition is a food, the honey can be present in an amount of about 0.001 wt % to about 10 wt % of the food, or even about 0.5 wt % to about 5 wt % of the food. In still other aspects, when the composition is a dietary supplement, the honey can be present in an amount of about 0.01 wt % to about 90 wt % of the supplement, or even about 1 wt % to about 75 wt % of the supplement.

Generally, the *spirulina* can be present in any therapeutically effect amount to controlling bad breath in an animal when combined with honey and generally depends on the form of composition to be administered. In a general embodiment, the *spirulina* can present in an amount of about 0.001 wt % to about 50 wt % of the composition. In some aspects, when the composition is a treat, the *spirulina* can be present in an amount of about 0.001 wt % to about 20 wt % of the treat, or even about 0.01 wt % to about 2 wt % of the treat, or in one specific aspect, about 0.1 wt % to about 1 wt %. In other aspects, when the composition is a food, the *spirulina* can be present in an amount of about 0.001 wt % to about 5 wt % of the food, or even about 0.01 wt % to about 2 wt % of the food. In still other aspects, when the composition is a dietary supplement, the *spirulina* can be present in an amount of about 0.01 wt % to about 75 wt % of the supplement, or even about 0.1 wt % to about 50 wt % of the supplement.

While the above amounts have been described in terms of specific compositions, such amounts can be used in other compositional forms including human food, human beverages, human supplements, pet foods, pet treats, pet supplements, etc. In one embodiment, the composition can be a pet treat. In another embodiment, the composition can be a supplement. In some aspects, the supplement can be a supplement for human consumption, or even a supplement for companion animal consumption. In one embodiment, the composition can be a food. In some aspects, the food can be a food for human consumption, or even a pet food. Additionally, in various aspects, such a pet food can be a wet pet food, a semi-moist pet food, or a dry pet food, e.g., kibble.

Generally, the present methods and compositions can be used for any animal. In one embodiment, the animal can be a human. In another embodiment, the animal can be a companion animal. In some aspect, the companion animal can be a dog, or even a cat.

Generally, the present methods and compositions can be administered to an animal for sufficient time to provide treatment, prevention, or minimization of bad breath in the animal. In one embodiment, the administration can be long-term administration. In another embodiment, the administration can be regular administration. In still another embodiment, the administration can be both long-term and regular administration. In one aspect, the composition can be administered to the animal weekly. In another aspect, the composition can be administered to the animal daily, and in one specific aspect, daily for at least one week. In some embodiments, the composition can be administered to the animal for a time period of at least one week, at least one month, at least two, three, four, five or six months; and in some embodiments, for at least one year. During the time period, the composition can be administered to the animal at least one day per week, at least two days per week, at least three, four, five or six days per week; or even seven days per week. The composition can be administered in a single dose per day or in multiple separate doses per day.

Generally, the composition comprises honey and *spirulina*. Additionally, the composition can further comprise a component selected from the group consisting of a protein, carbohydrates, fat, and mixtures thereof. Further, the composition can include other health promoting additives or ingredients. Such additives or ingredients can include one or more of vitamins, omega-3 fatty acids, antioxidants, minerals, amino acids, medium chain triglycerides, etc.

Non-limiting examples of suitable omega-3 fatty acids include eicosapentaenoic acid (EPA), docosahexaenoic acid (DHA), alpha-linolenic acid (ALA) and mixtures thereof. In one embodiment, the omega-3 fatty acids can range from about 0.2 wt % to about 3 wt % of the composition. In some embodiments, the omega-3 fatty acids are at least about 0.2 wt %, at least about 1.0 wt %, or at least about 2.0 wt %.

Non-limiting examples of suitable amino acids include free amino acids, methionine, cysteine, homocysteine, taurine and mixtures thereof.

Non-limiting examples of vitamins include A, B-complex (such as B-1, B-2, B-6 and B-12), C, D, E and K, niacin and acid vitamins such as pantothenic acid and folic acid and biotin.

Non-limiting examples of minerals include calcium, iron, zinc, magnesium, iodine, copper, phosphorus, manganese, potassium, chromium, molybdenum, selenium, nickel, tin, silicon, vanadium and boron.

Non-limiting examples of antioxidants include beta-carotene, vitamin C, vitamin E, and selenium, or any compound that inhibit oxidation or reactions promoted by Reactive Oxygen Species (ROS) and other radical and non-radical species. Additionally, antioxidants are molecules capable of slowing or preventing the oxidation of other molecules. Non-limiting examples of antioxidants include carotenoids, coenzyme Q10 ("CoQ10"), flavonoids, glutathione Goji (Wolfberry), hesperidine, Lactowolfberry, lignan, lutein, lycopene, polyphenols, selenium, vitamin A, vitamin B1, vitamin B6, vitamin B12, vitamin C, vitamin D, and vitamin E.

The pet food compositions disclosed herein can be any food formulated for consumption by a pet, such as a dog. In an embodiment, the pet food composition provides complete nutrition as defined by the Association of American Feed Control Officials (AAFCO) and which depends on the type of animal for which the composition is intended (e.g., a dog). In another embodiment, the composition can be a supplement. Such a supplement can be added to a food composition or be administered in conjunction with a food composition, or administered separately.

In one embodiment, the food compositions can comprises the protein in amounts from about 30%, 35%, 40%, 45%, 50%, 55%, or even 60% to about 35%, 40%, 45%, 50%, 55%, 60%, or even 65%, including various subranges within these amounts. In one aspect, the protein can be from about 45% to about 55% of the food composition.

The pet food composition can comprise meat, such as emulsified meat. Examples of suitable meat include poultry, beef, pork, lamb and fish, especially those types of meats suitable for pets. The meat can include any additional parts of an animal including offal. Some or all of the meat can be provided as one or more meat meals, namely meat that has been dried and ground to form substantially uniform-sized particles and as defined by AAFCO. Additionally or alternatively, vegetable protein can be used, such as pea protein, corn protein (e.g., ground corn or corn gluten), wheat protein (e.g., ground wheat or wheat gluten), soy protein (e.g., soybean meal, soy concentrate, or soy isolate), rice protein (e.g., ground rice or rice gluten) and the like.

In one embodiment, the food compositions can comprises the fat in amounts from about 10%, 15%, 20%, 25%, 30%, or even 35% to about 15%, 20%, 25%, 30%, 35%, or even 40%, including various subranges within these amounts. In one aspect, the fat comprises from about 25% to about 35% of the food composition.

The pet food compositions disclosed herein can comprise one or more of a vegetable oil, a flavorant, a colorant or water. Non-limiting examples of suitable vegetable oils include soybean oil, corn oil, cottonseed oil, sunflower oil, canola oil, peanut oil, safflower oil and the like. In some embodiments, the lipids in the composition can consist of the medium chain triglycerides (MCTs) and one or more of any vegetable oil, any fish oil, the lipid from any meat, and any omega-3 fatty acids.

Non-limiting examples of suitable flavorants include yeast, tallow, rendered animal meals (e.g., poultry, beef, lamb, pork), flavor extracts or blends (e.g., grilled beef), animal digests, and the like. Non-limiting examples of suitable colorants include FD&C colors, such as blue no. 1, blue no. 2, green no. 3, red no. 3, red no. 40, yellow no. 5, yellow no. 6, and the like; natural colors, such as caramel coloring, annatto, chlorophyllin, cochineal, betanin, turmeric, saffron, paprika, lycopene, elderberry juice, pandan, butterfly pea and the like; titanium dioxide; and any suitable food colorant known to the skilled artisan.

The pet food compositions disclosed herein can optionally include additional ingredients, such as starches, humectants, oral care ingredients, preservatives, amino acids, fibers, prebiotics, sugars, animal oils, aromas, other oils additionally or alternatively to vegetable oil, salts, vitamins, minerals, probiotic microorganisms, bioactive molecules or combinations thereof.

In one embodiment, the food compositions can comprises the carbohydrate in amounts from about 10%, 15%, 20%, 25%, 30%, 35%, 40%, 45%, 50%, 55%, 60%, 65%, 70%, or even 75% to about 10%, 15%, 20%, 25%, 30%, 35%, 40%, 45%, 50%, 55%, 60%, 65%, 70%, 75%, 80%, 85%, or even 90%, including various subranges within these amounts. In one aspect, the carbohydrate comprises from about 25% to about 50% of the food composition.

Non-limiting examples of suitable starches include a grain such as corn, rice, wheat, barley, oats, potatoes, peas, beans, cassava, and the like, and mixtures of these grains, and can be included at least partially in any flour. Non-limiting examples of suitable humectants include salt, sugars, propylene glycol and polyhydric glycols such as glycerin and sorbitol, and the like. Non-limiting examples of suitable oral care ingredients include alfalfa nutrient concentrate containing chlorophyll, sodium bicarbonate, phosphates (e.g., tricalcium phosphate, acid pyrophosphates, tetrasodium pyrophosphate, metaphosphates, and orthophosphates), peppermint, cloves, parsley, ginger and the like. Non-limiting examples of suitable preservatives include potassium sorbate, sorbic acid, sodium methyl para-hydroxybenzoate, calcium propionate, propionic acid, and combinations thereof.

The food compositions may also comprise one or more fiber sources. The term "fiber" includes all sources of "bulk" in the food whether digestible or indigestible, soluble or insoluble, fermentable or nonfermentable. Such fibers can be from plant sources such as marine plants but microbial sources of fiber may also be used. A variety of soluble or insoluble fibers may be utilized, as will be known to those of ordinary skill in the art. The fiber source can be beet pulp (from sugar beet), gum arabic, gum talha, psyllium, rice bran, carob bean gum, citrus pulp, pectin, fructooligosaccharide, short chain oligofructose, mannanoligofructose, soy fiber, arabinogalactan, galactooligosaccharide, arabinoxylan, or mixtures thereof.

Alternatively, the fiber source can be a fermentable fiber. Fermentable fiber has previously been described to provide a benefit to the immune system of a companion animal. Fermentable fiber or other compositions known to skilled artisans that provide a prebiotic to enhance the growth of probiotics within the intestine may also be incorporated into the composition to aid in the enhancement of the benefits described herein or to the immune system of an animal.

In some embodiments, the ash content of the food composition ranges from less than 1% to about 15%. In one aspect, the ash content can be from about 5% to about 10%.

Specific amounts for each additional ingredient in the pet food compositions disclosed herein will depend on a variety of factors such as the ingredient included in the first edible material and any second edible material; the species of animal; the animal's age, body weight, general health, sex, and diet; the animal's consumption rate; the purpose for which the food product is administered to the animal; and the like. Therefore, the components and their amounts may vary widely.

Yet another aspect of the present disclosure is a method of making a composition, the method comprising adding honey and *spirulina* to at least one other comestible ingredient, the honey and *spirulina* are added in a therapeutically effective amount to prevent or treat or minimize bad breath in an animal.

EXAMPLE

By way of example and not limitation, the following non-limiting study is illustrative of compositions and methods using honey and *spirulina* for treating, preventing, or minimizing bad breath in an animal, in one or more embodiments provided by the present disclosure.

Example 1—In Vitro Study for Canines

Saliva samples were collected from 6-10 dogs (Labrador retrievers and English Setter) for testing of volatile sulfur compounds (VSC) including hydrogen sulfide ($H_2S$), methyl mercaptan ($CH_3SH$), and dimethyl sulfide (($CH_3)_2S$), all of which were measured using a portable gas chromatograph, OralChroma (available from Nissha FIS, Inc.). Each sample was prepared by adding 115 mg of the ingredient, or combined ingredients (50:50 ratio), to 10 ml water and held overnight to allow for hydration. Saliva was then added to the sample in an amount of 0.5 ml and the sample was then kept at 37° C. for 24 hours. A blank was also prepared having no ingredient. Two rounds were performed, each having two samples that were run in duplicate for each ingredient. The samples and average results (ng/10 ml) are shown in table 1.

TABLE 1

| | Round 1 | | | | Round 2 | | | |
|---|---|---|---|---|---|---|---|---|
| Ingredients | $H_2S$ (ng/10 ml) | $CH_3SH$ (ng/10 ml) | $(CH_3)_2S$ (ng/10 ml) | Total* VSC (ng/10 ml) | $H_2S$ (ng/10 ml) | $CH_3SH$ (ng/10 ml) | $(CH_3)_2S$ (ng/10 ml) | Total* VSC (ng/10 ml) |
| Blank | 8.87 | 4.65 | 13.00 | 26.51 | 0.00 | 1.08 | 21.30 | 22.38 |
| Honey | 26.58 | 0.00 | 5.33 | 31.91 | 0.00 | 4.69 | 17.42 | 22.11 |
| Spirulina | 26.58 | 80.15 | 8.59 | 115.32 | 26.58 | 80.15 | 14.71 | 121.44 |
| Honey + Spirulina | 0.00 | 8.11 | 20.86 | 28.97 | 14.42 | 1.78 | 8.64 | 24.84 |

*Total VSC is the combined amounts of hydrogen sulfide, methyl mercaptan, and dimethyl sulfide As shown in Table 1, the combination of honey and *spirulina* provides synergistic effects. In Round 1, hydrogen sulfide was unexpectedly decreased by the combination of honey and *spirulina* as compared to each individual ingredient that actually increased the level of hydrogen sulfide when tested separately. In Round 2, dimethyl sulfide was decreased by 59.4% over the blank, more than the additive effect of honey (18.2%) and *spirulina* (30.9%) when measured separately. In Rounds 1 and 2, both methyl mercaptan and total VSCs provided synergistic data for the combination of honey and *spirulina* as compared to when each ingredient was tested separately.

Example 2—In Vivo Study for Canines 64 dogs were tested in four distinct groups (each group consisting of 16 dogs), no treat, dental dog treat (Dentalife® by Nestle Purina Petcare Company), a treat supplemented with honey, and a treat supplemented with honey and *spirulina*. Formulations are provided in Table 2. Samples were collected and prepared by inserting a 1 ml syringe into the dog's mouth and drawing back mouth air when the dogs mouth was closed and measured using a portable gas chromatograph, OralChroma (available from Nissha FIS, Inc.). The results are shown in Table 3.

TABLE 2

| Ingredients | Dentalife ® | Honey | Honey + Spirulina |
|---|---|---|---|
| Protein (%) | 10.3 | 8.9 | 9.3 |
| Fat (%) | 3.4 | 3.1 | 3.2 |
| Carbohydrate (%) | 72.0 | 74.3 | 72.9 |
| Fiber (%) | 0.2 | 0.3 | 0.6 |
| Moisture (%) | 11.8 | 11.2 | 12.1 |
| Honey (%) | — | 1.4 | 1.4 |
| Spirulina (%) | — | — | 0.2 |

TABLE 3

| Treat | Week | $H_2S$ (ng/10 ml) | $CH_3SH$ (ng/10 ml) | $(CH_3)_2S$ (ng/10 ml) | Total* VSC (ng/10 ml) |
|---|---|---|---|---|---|
| No Treat | 0** | 0 | 0 | 0 | 0 |
| | 1 | −0.18 | −0.29 | −0.59 | −1.06 |
| | 2 | −0.11 | −1.51 | −6.47 | −8.09 |
| | 3 | −0.92 | −1.58 | −4.01 | −6.51 |
| | 4 | −0.55 | −2.55 | −5.73 | −8.82 |
| Dentalife ® | 0** | 0 | 0 | 0 | 0 |
| | 1 | −1.14 | −1.83 | −5.17 | −8.14 |
| | 2 | −0.68 | −2.05 | −9.01 | −11.74 |
| | 3 | −1.17 | −2.91 | −8.05 | −12.14 |
| | 4 | −1.23 | −2.71 | −7.10 | −11.04 |
| Honey Treat | 0 | 0 | 0 | 0 | 0 |
| | 1 | −0.13 | −1.83 | −2.06 | −4.02 |
| | 2 | −0.08 | −1.72 | −7.78 | −9.58 |
| | 3 | −0.73 | −3.90 | −5.55 | −10.18 |
| | 4 | −0.30 | −4.23 | −7.04 | −11.56 |
| Honey + Spirulina Treat | 0 | 0 | 0 | 0 | 0 |
| | 1 | −0.75 | −6.77 | −3.17 | −10.69 |
| | 2 | −1.71 | −6.56 | −6.95 | −15.22 |
| | 3 | −1.35 | −8.05 | −7.36 | −16.76 |
| | 4 | −1.85 | −8.14 | −7.44 | −17.43 |

*Total VSC is the combined amounts of hydrogen sulfide, methyl mercaptan, and dimethyl sulfide
**Week 0 is baseline, which is set to zero with all subsequent measurements showing change from baseline As shown in Table 3, canines given the honey and *spirulina* treat showed far superior results than the dental treat or the treat supplemented with honey.

Example 3—In Vivo Study for Canines 43 dogs were tested in three distinct groups, honey treat (15 dogs), *spirulina* treat (14 dogs), and combination treat (14 dogs), the treats were fed daily to the dogs and malodor data was collected. Formulations are provided in Table 3. Samples were collected and prepared by inserting a 1 ml syringe into the dog's mouth and drawing back mouth air when the dogs mouth was closed and measured using a portable gas chromatograph, OralChroma (available from Nissha FIS, Inc.). The results are shown in Table 4.

TABLE 3

| Ingredients | Honey | Spirulina | Honey + Spirulina |
|---|---|---|---|
| Protein (%) | 10.3 | 8.9 | 9.3 |
| Fat (%) | 3.4 | 3.1 | 3.2 |
| Carbohydrate (%) | 72.0 | 74.3 | 72.9 |
| Fiber (%) | 0.2 | 0.3 | 0.6 |
| Moisture (%) | 11.8 | 11.2 | 12.1 |
| Honey (%) | 1.4 | — | 1.4 |
| Spirulina (%) | — | 0.2 | 0.2 |

TABLE 4

| Treat | Week | $H_2S$ (ng/10 ml) | $CH_3SH$ (ng/10 ml) | $(CH_3)_2S$ (ng/10 ml) | Total* VSC (ng/10 ml) |
|---|---|---|---|---|---|
| Honey | 0** | 0 | 0 | 0 | 0 |
| | 1 | −0.007 | −0.098 | 0.330 | 0.225 |
| | 2 | −0.005 | −0.099 | −0.075 | −0.178 |
| | 3 | 0.023 | −0.060 | 0.779 | 0.742 |
| | 4 | −0.003 | −0.094 | −0.487 | −0.585 |
| | 5 | 0.011 | −0.098 | −0.802 | −0.889 |

TABLE 4-continued

| Treat | Week | $H_2S$ (ng/10 ml) | $CH_3SH$ (ng/10 ml) | $(CH_3)_2S$ (ng/10 ml) | Total* VSC (ng/10 ml) |
|---|---|---|---|---|---|
| | 6 | 0.172 | −0.088 | −0.320 | −0.235 |
| | 7 | 0.532 | −0.054 | 0.035 | 0.513 |
| | 8 | 0.270 | −0.093 | −0.256 | −0.079 |
| Spirulina | 0** | 0 | 0 | 0 | 0 |
| | 1 | −0.010 | 0.031 | 0.191 | 0.213 |
| | 2 | −0.039 | 0.203 | 0.177 | 0.341 |
| | 3 | 0.035 | 0.203 | 0.955 | 1.193 |
| | 4 | −0.001 | 0.110 | −0.165 | −0.056 |
| | 5 | −0.013 | 0.014 | −0.304 | −0.303 |
| | 6 | 0.199 | 0.081 | −0.194 | 0.086 |
| | 7 | 0.675 | 0.129 | 0.357 | 1.161 |
| | 8 | 0.431 | 0.056 | −0.003 | 0.484 |
| Honey + Spirulina | 0** | 0 | 0 | 0 | 0 |
| | 1 | 0.004 | −0.070 | 0.367 | 0.302 |
| | 2 | 0.013 | 0.013 | −0.127 | −0.100 |
| | 3 | 0.035 | 0.060 | 0.485 | 0.579 |
| | 4 | 0.009 | −0.005 | −0.480 | −0.475 |
| | 5 | 0.022 | −0.035 | −0.250 | −0.263 |
| | 6 | 0.362 | 0.008 | −0.238 | 0.132 |
| | 7 | 0.631 | 0.050 | 0.392 | 1.073 |
| | 8 | 0.481 | 0.009 | −0.422 | 0.068 |
| Expected Additive | 0** | 0 | 0 | 0 | 0 |
| | 1 | −0.017 | −0.066 | 0.521 | 0.438 |
| | 2 | −0.043 | 0.105 | 0.102 | 0.163 |
| | 3 | 0.058 | 0.143 | 1.735 | 1.935 |
| | 4 | −0.004 | 0.015 | −0.652 | −0.641 |
| | 5 | −0.002 | −0.084 | −1.106 | −1.192 |
| | 6 | 0.371 | −0.007 | −0.514 | −0.150 |
| | 7 | 1.207 | 0.075 | 0.392 | 1.674 |
| | 8 | 0.701 | −0.038 | −0.259 | 0.405 |

*Total VSC is the combined amounts of hydrogen sulfide, methyl mercaptan, and dimethyl sulfide
**Week 0 is baseline, which is set to zero with all subsequent measurements showing change from baseline As seen in Table 4, the present combination of honey and *spirulina* provided synergistic results for hydrogen sulfide, methyl mercaptan, dimethyl sulfide, and total volatile sulfur compounds when compared to the expected additive effect. The preset combination treat reduced volatile sulfur compounds more effectively than expected based on using honey or *spirulina* alone.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of treating bad breath in a canine comprising administering to a canine in need thereof an effective amount of a composition comprising 0.001 to 10 wt % of honey and 0.001 to 10 wt % *spirulina*.

2. The method of claim 1, wherein the honey is present in an amount of about 0.001 wt % to about 5 wt % of the composition.

3. The method of claim 1, wherein the *spirulina* is present in an amount of about 0.001 wt % to about 5 wt % of the composition.

4. The method of claim 1, wherein the composition further comprises a component selected from the group consisting of a protein, carbohydrates, fat, and mixtures thereof.

5. The method of claim 1, wherein the composition is a a pet food, a pet treat, or a supplement.

6. The method of claim 1, wherein the composition is a pet treat.

7. The method of claim 1, wherein the composition is administered to the canine daily for at least one week.

* * * * *